(12) United States Patent
Dziak et al.

(10) Patent No.: US 9,427,378 B2
(45) Date of Patent: Aug. 30, 2016

(54) GASTRIC JEJUNAL TUBE WITH AN ENLARGED JEJUNAL LUMEN

(71) Applicant: AVENT, INC., Alpharetta, GA (US)

(72) Inventors: Katherine L. Dziak, Cumming, GA (US); Donald J. McMichael, Roswell, GA (US); Michael A. Schmidt, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 216 days.

(21) Appl. No.: 14/089,038

(22) Filed: Nov. 25, 2013

(65) Prior Publication Data

US 2014/0323966 A1     Oct. 30, 2014

Related U.S. Application Data

(60) Provisional application No. 61/817,549, filed on Apr. 30, 2013.

(51) Int. Cl.
*A61M 15/00* (2006.01)
*A61J 15/00* (2006.01)

(52) U.S. Cl.
CPC ......... *A61J 15/0049* (2013.01); *A61J 15/0015* (2013.01); *A61J 15/0042* (2013.01); *A61J 15/0069* (2013.01); *A61J 15/0073* (2013.01); *A61J 15/0038* (2013.01); *A61J 15/0065* (2013.01); *A61M 2210/1053* (2013.01); *A61M 2210/1057* (2013.01)

(58) Field of Classification Search
CPC ............. A61J 15/0042; A61J 15/0069; A61J 15/0046; A61J 15/0038; A61J 15/0073; A61J 15/0065; A61J 15/0015; A61J 15/0026; A61J 15/0076–15/0088; A61M 16/041; A61M 25/0032; A61M 25/0035; A61M 25/0037; A61M 39/0247; A61M 2039/085; A61M 2039/0261; A61M 2210/1057; A61M 2210/1053; A61M 2210/07

See application file for complete search history.

(56) References Cited

U.S. PATENT DOCUMENTS

| | | | | |
|---|---|---|---|---|
| 4,995,865 | A | * | 2/1991 | Gahara ............. A61M 25/0026 604/43 |
| 5,261,879 | A | * | 11/1993 | Brill .................... A61M 25/104 604/913 |
| 6,019,746 | A | | 2/2000 | Picha et al. |
| 2002/0072705 | A1 | * | 6/2002 | Vrba ....................... A61F 2/958 604/96.01 |
| 2003/0225369 | A1 | * | 12/2003 | McMichael ......... A61J 15/0015 604/104 |
| 2006/0184097 | A1 | * | 8/2006 | Quinn ............. A61M 25/09025 604/43 |
| 2008/0097350 | A1 | * | 4/2008 | Bell .................. A61M 25/0023 604/266 |
| 2009/0270801 | A1 | * | 10/2009 | Shimada ........... A61M 25/0023 604/96.01 |
| 2011/0098660 | A1 | * | 4/2011 | Porreca, Jr. ....... A61M 25/0026 604/246 |
| 2012/0089128 | A1 | | 4/2012 | Rotella et al. |
| 2012/0203171 | A1 | * | 8/2012 | Williams ............ A61J 15/0015 604/96.01 |

FOREIGN PATENT DOCUMENTS

EP      2 486 911 A2    8/2012

* cited by examiner

*Primary Examiner* — Imani Hayman
*Assistant Examiner* — Jenna Zhang
(74) *Attorney, Agent, or Firm* — Dority & Manning, P.A.

(57) ABSTRACT

The present disclosure describes a gastric jejunal tube having a gastric lumen and a jejunal lumen that run the length of the tube. The cross-sectional sizes of the lumens change from above to below the most distal gastric port. A method of making the gastric jejunal tube is also described.

10 Claims, 2 Drawing Sheets

GASTRIC JEJUNAL TUBE WITH AN ENLARGED JEJUNAL LUMEN

This application claims priority from U.S. provisional patent application 61/817,549 filed on Apr. 30, 2013.

The present disclosure relates to a gastric jejunal feeding tube used in patients that need nutrition delivered directly to the jejunum.

Enteral feeding may be necessary because of a number of causes, one of which is the not uncommon reaction following major surgery in which a patient's stomach function is impaired for a period of time. If the patient has a problem with gastric reflux or vomiting, for example, or if the stomach is not adequate for the patient's digestive process requirements, another feeding mode must be chosen. In addition to the need to supply or supplement the body with a certain level of nutrients and the like following surgery as well as in other instances of impaired or limited gastric functionality, a further issue is that an unfed gut can become a source of bacteria that gets into the bloodstream. These types of problems may be resolved by the introduction of nutrients through an enteral feeding device tube properly inserted through the patient's abdominal wall, gastric wall, pylorus, duodenum, and/or into the jejunum beyond the Ligament of Treitz.

Many patient feeding devices employ a gastrostomy feeding tube. One relatively common situation is to provide nutritional solutions or medicines directly into the stomach or intestines. A stoma is formed in the stomach or intestinal wall and a catheter is placed through the stoma. Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. U.S. Pat. No. 6,019,746 provides an example of such a device.

Methods of jejunal feeding involve an extended length tube through a stoma in the stomach, past the pyloric sphincter, through the duodenum and into the jejunum. Placement of such an extended tube is a challenging task because of the many twists and turns between the stomach and jejunum. This is a particular challenge because of the sharp bend at the ligament of Treitz between the duodenum and jejunum.

Placement of the extended tube may use a catheter device that is inserted into the patient through a surgically prepared stoma created in the abdominal wall using traditional surgical procedures. These types of procedures include Stamms Gastrostomy, Witzel Gastrostomy, and others. A growing number of extended tubes are placed using procedures that involve percutaneous gastrostomy. Percutaneous gastrostomy involves the suturing of the stomach to the abdominal wall (gastropexy), and the creation of a stoma using an introducer needle, dilation, and appropriate placement devices. After the stoma is created, the extended feeding tube may be placed over a properly positioned guide wire. Endoscopic devices can aid in visualizing the placement of the guide wires and the extended tubes; interventional radiologists may also place jejunal feeding tubes using fluoroscopy and computed tomography visualization techniques.

While current techniques for placing an extended feeding tube through a stoma in the stomach and into the jejunum are adequate, it has been found that maintaining the device in place in a stable manner in the patient can be difficult. The reason for this is the peristaltic action of the muscles of the intestinal tract which can result in the distal portions of the extended tube being moved upwardly (migrating) towards the stomach. Should this occur, it requires replacement of the tube in the jejunum and that involves another procedure with its concomitant risks to the patient.

Another issue with current gastric jejunal tubing is the shape of the various lumens within the tubing. There are generally three lumens: an inflation lumen to provide water to a retention balloon (located on the tubing) that is used to keep the head of the device in place against the skin; a jejunal lumen to provide nutrition; and a gastric lumen to deliver medication and aspirate the stomach. Currently used silicone tubing has lumens with numerous sharply angled corners that can clog with feeding solution or collapse. These lumens can also impede the advance of guide wires because of their shape and narrow cross-section.

An attempted solution to prevent migration of distal portions of the extended tube has been the use of filler in a portion of the jejunal tube to help to stiffen it so that it is less affected by peristaltic action and is more likely to stay where it is placed. While this approach has been effective to a degree, the stiffer jejunal tube requires a larger outer diameter (OD) to provide it sufficient flexibility but which can cause obstructions and irritation in the bowels or intestines and must also have a smaller diameter internal feeding lumen for the delivery of nutrients, which can easily clog. Larger OD tubes are particularly problematic in pediatric applications for obvious reasons.

A stiffer tube is also more difficult to thread from the stomach to the jejunum. The ligament of Treitz, between the duodenum and jejunum, includes a very sharp bend. A stiff tube is quite difficult to thread through this bend and may, particularly for smaller or pediatric patients, distort the anatomy and cause irritation and discomfort.

Alternatively, a weight at the distal end of the tube has been used in an effort to keep the extended jejunal tube in place. While such a tube is not as stiff, it also has a relatively small jejunal lumen which may clog and the weight is often not enough to keep the tube in place.

Rather than use an extended length tube, another prior art solution has been to insert a short feeding tube directly into a stoma in the jejunum. While this is effective in delivering nutrients to the jejunum it involves a different and more involved surgical procedure than those that feed the tube into the stomach and then into the jejunum. This procedure has higher risk of complications for the patient and so is not preferred.

What is needed is a gastric jejunal feeding tube (GJ tube) that may be inserted into a stoma in the stomach, extended through the pyloric sphincter, the duodenum, past the ligament of Treitz and into the jejunum, and that will remain in place for an extended time without being displaced upwardly back into the stomach. Also needed is a GJ tube that will not clog as easily as current tubes and that will provide a jejunal lumen with a large cross-sectional area downstream of the port that marks the functional end of the gastric lumen.

SUMMARY

The present disclosure describes a gastric jejunal tube (GJ tube) having: a jejunal lumen, a functional gastric lumen, a non-functional gastric lumen, and, for those embodiments that include an inflatable balloon, a functional balloon lumen, a non-functional balloon lumen. When a retention component other than a balloon is used, the balloon lumens are omitted. The non-functional lumens are reduced in cross-sectional size from a point below the most distal gastric port to the distal end of the GJ tube. The functional lumens respectively join to the non-functional lumens at a point below the most distal gastric port. The jejunal, functional and non-functional lumens are contained within a single extended length tubing structure. The jejunal lumen traverses the entire GJ tube and has a first cross-sectional area above the gastric port(s) and at least a second cross-sectional area that is different from the first and is below the most distal gastric port; the second cross-sectional is desirably larger than the first. The jejunal lumen terminates in at least one jejunal port at or near the distal end of the GJ tube. The gastric port(s) allows delivery of medication and/or nutrients to the stomach or aspiration of gastric contents, if desired, by providing fluid communication between the stomach and the functional gastric lumen and there may be more than one gastric port. The non-functional lumens are held in reduced size states, desirably by an adhesive. Suitable examples of adhesives are curable or temperature sensitive ones. The addition of tungsten to the adhesive helps provide visibility under fluoroscopy. The GJ tube is desirably made from polyurethane.

A method of making the gastric jejunal tube is also described. In the method, a plastic tube having a jejunal lumen, a gastric lumen and, optionally a balloon lumen is subjected to the steps, in no particular order, of pressurizing the jejunal lumen of the tube, adding adhesive to selected portions of the other lumens, e.g., the balloon and/or gastric lumens below the most distal gastric port, solidifying the adhesive, and, releasing the pressure from the jejunal lumen. Pressurizing the jejunal tube changes (increases) the cross-sectional size of the jejunal tube relative to the other lumen(s). The tube may be constrained in a cylindrical fixture during the steps of pressurizing, adhesive adding and solidifying in order to maintain a uniform exterior shape and/or dimension, i.e., OD, for substantially all of the GJ tube.

In addition, radio-opaque materials may be added to the GJ tube and/or adhesive to aid in placement of the GJ tube and to allow monitoring of its location within the body via CT scans, X-ray images, and the like.

Other objects, advantages and applications of the present disclosure will be made clear by the following detailed description of a preferred embodiment of the disclosure and the accompanying drawings wherein reference numerals refer to like or equivalent structures.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

In jejunal feeding it is desired to place the distal end or "tail" of the feeding tube in the jejunum where nutrients are desired to be delivered. As described above, the tube is inserted into and through the stomach, into and through the duodenum and beyond the ligament of Treitz and into the jejunum. Passing the tube beyond the ligament of Treitz is particularly challenging because this ligament induces a sharp bend in the duodenum. A very stiff tube will have difficulty in rounding this sharp bend, while an overly flexible tube will be easily displaced upward into the stomach through peristaltic action and may kink. The disclosed device addresses these challenges.

Figure 1:
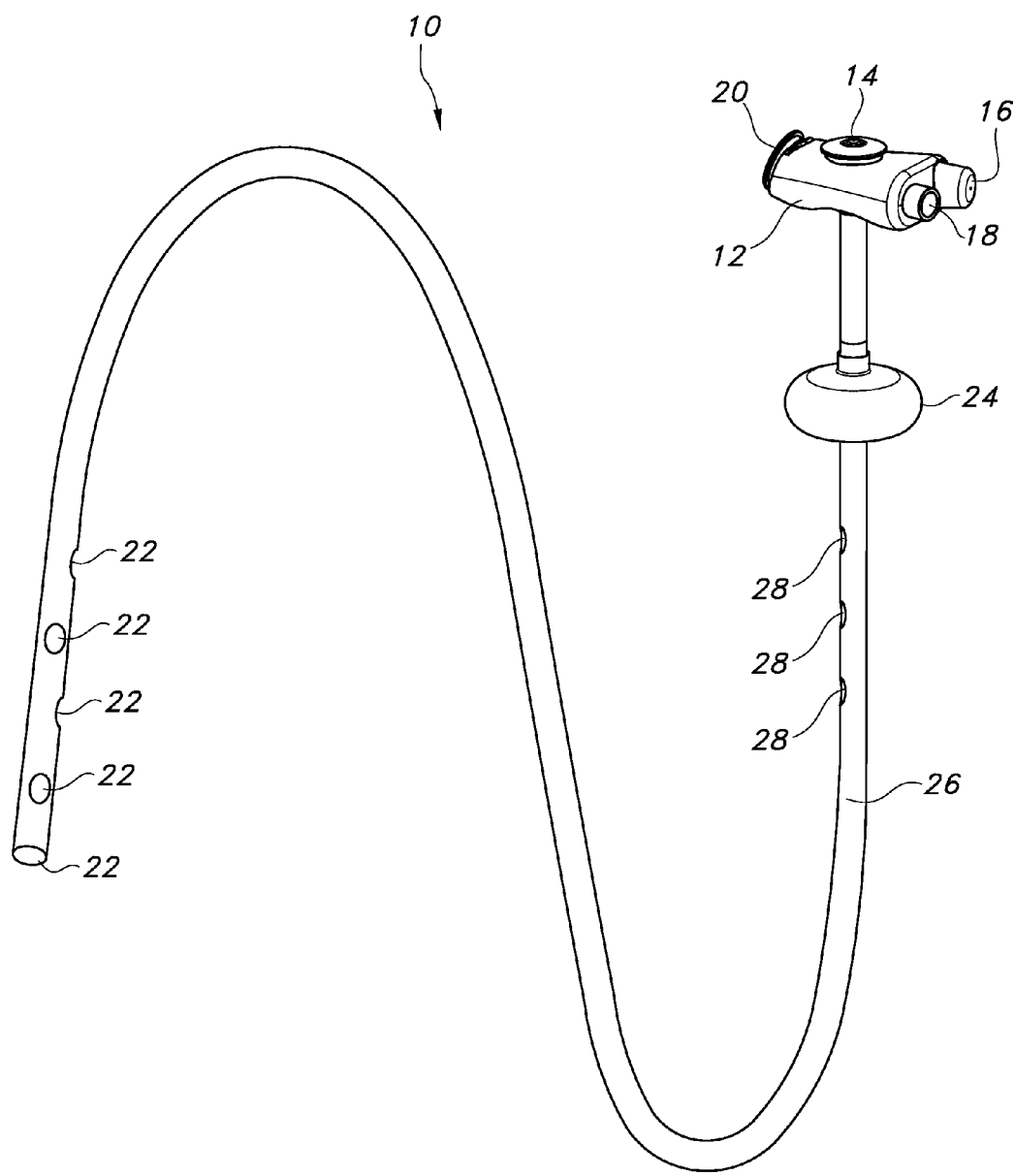
FIG. 1 is a view of a gastric jejunal tube device showing a general arrangement of a tube device for delivering nutrients to the jejunum.

Turning to the drawings, FIG. 1 illustrates an embodiment of a gastric jejunal tube enteral feeding device 10 having an extended length tube 26 and a base 12. The GJ tube 26 has a balloon lumen used to inflate a retention balloon 24, a jejunal lumen used to provide nutrition to the jejunum through at least one jejunal port(s) 22 at or near the distal end 29 of the tube, and a gastric lumen used to deliver medication through at least one gastric port(s) 28 to the stomach and to aspirate the stomach. The lumens run the entire length of the tube 26.

The device 10 of FIG. 1 has a base 12 that remains outside and adjacent to the patient's body and through which nutrients are provided to the patient. The base 12 has a proximal side and a distal side. The tube 26 is joined to the base 12 and extends away from the base 12 on the distal side to form the device/assembly 10. The distal side of the device 10 often includes a locking means or retention device, e.g., a balloon 24, or a mechanically actuated retention device (not shown) which may be expanded inside the body to hold the device 10 in a desired position in a body cavity, such as a stomach lumen, after it is installed. Mechanically actuated retention devices include "pigtails", bumpers and other means known to those skilled in the art. It should be noted that the gastric-jejunal tube 26 disclosed herein may be used with virtually any base or locking means known in the art, not just those mentioned here. In addition, at least one gastric port 28 on the gastric lumen 36, 46 below the retention device allows access to the stomach for dispensing medication or for aspiration of the stomach.

Figure 2:
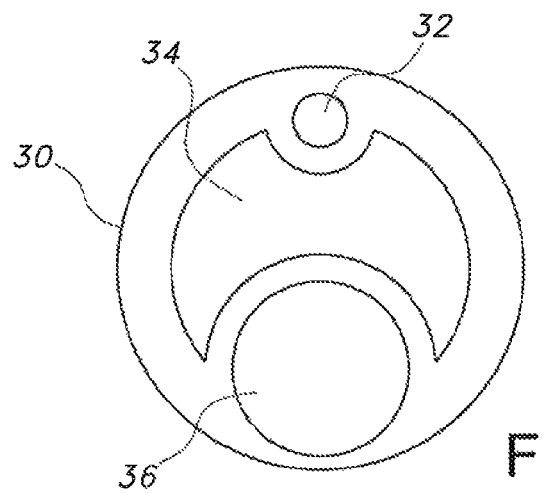
FIG. 2 is a cross-sectional view of the prior art silicone gastric jejunal feeding tube.

As can be seen in FIG. 2, the cross-sectional shape of a prior art tube 30 shows a round balloon lumen 32 used to inflate the balloon 24 via delivery of a fluid, usually water, a "bat wing" shaped jejunal lumen 34 used to provide nutrition to the jejunum, and a round gastric lumen 36 used to deliver medication, nutrition, water, etc. to the stomach and aspirate the stomach. The prior art tube 30 has the same cross-sectional area for its entire length, i.e. above and below the gastric port(s). Since the jejunal lumen typically extends for up to 60 cm past the gastric port 28 to its distal end 29, while the tubing in the gastric area is at most 25 cm long and often only 4-6 cm long, the prior art jejunal lumen 34 has a tendency to clog in the sharply angled corners and can be an impediment to the successful advancement of a guide wire. The nutrition going into the intestine is normally administered very slowly and as the body warms the nutrition it can cause it to 'curdle' in the lumen, thus causing clogs. Clogs can also be caused for a variety of other reasons (acid, bacteria, etc). As the nutrients travel along the length of the jejunal lumen, therefore, there is greater and greater risk of the formula curdling or clogging the tube. It is important to have as much open cross-sectional area as possible, particularly below the gastric ports because of the greater length below the ports and the greater chance of clogging.

Figure 3:
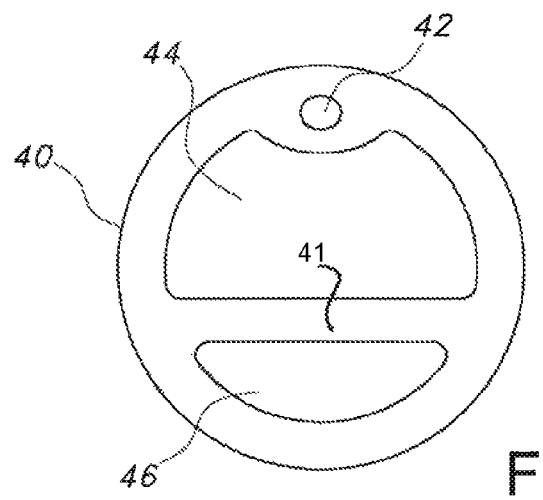
FIG. 3 is a cross-sectional view of the disclosed gastric-jejunal feeding tube prior to the addition of adhesive and above the gastric port.

One embodiment of the disclosed gastric-jejunal tube 26 has a cross-section 40 above the gastric port(s) as shown in FIG. 3. This portion of the tube 26 has functional gastric 46, balloon 42, and jejunal 44 lumens. An interior wall 41 separates the gastric lumen 46 and the jejunal lumen 44. The balloon inflation lumen 42 can be slightly modified to a more oval shape or to a round shape and the gastric lumen 46 can have a "D"shape. This tube may be made by conventional extrusion known to those skilled in the art.

Figure 4:
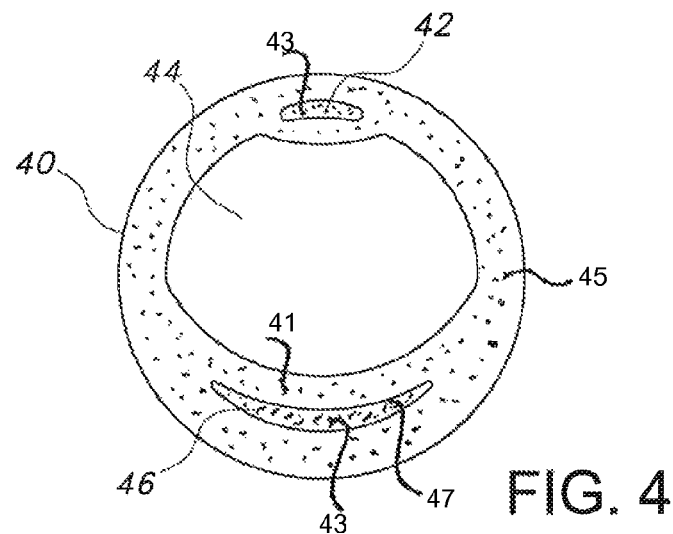
FIG. 4 is a cross-sectional view of the disclosed gastric-jejunal tube below the gastric port where adhesive has been added and solidified and the lumens are different from FIG. 3.

FIG. 4 shows the cross-section of the disclosed gastric-jejunal tube 26 below the most distal gastric port where the interior wall 41 changes or shifts position. This portion of the tube 26 has a non-functional gastric lumen 46 and a non-functional balloon inflation lumen 42 but provides a larger (functional) jejunal lumen 44 below the most distal gastric port 28 to its distal end 29. The respective functional and non-function lumens join together so that the gastric and balloon lumens run the entire length of the tube.

The point at which the jejunal lumen changes from a first cross-sectional area to a second cross-sectional area and where the functional and non-functional lumens respectively join ranges from just below the most distal gastric port to approximately 5 cm below the most distal gastric port.

To increase the open area of the jejunal lumen 44 below the most distal gastric port 28, a process for closing the gastric lumen 46 and optionally the balloon inflation lumen 42 with adhesive 43 was developed. In this process, the jejunal lumen 44 is pressurized with fluid (e.g. air or nitrogen) to a pressure from 5 to 15 psi (34.5 to 103.4 kilopascal) to enlarge its cross-sectional area and to reduce the size of, or at least partially collapse, the other lumens, adhesive is added to the gastric lumen 46 and optionally the balloon inflation lumen 42, and the adhesive is solidified. The adhesive may be added prior to or after the jejunal lumen 44 is pressurized, though desirably before. The gastric and balloon lumens 46, 42 may be open to the atmosphere while the jejunal lumen 44 is pressurized. In one embodiment, the adhesive fills the designated lumen(s) from approximately just below the gastric lumen port(s) 28 to the distal end 29 of the tube.

In another embodiment the adhesive may be discontinuously placed or spaced apart within the gastric and/or balloon lumens 46, 42, perhaps allowing more flexibility in one zone of the tube 26 over another while maintaining closure of the lumens 46, 42 between the locations of the adhesive. In all embodiments, the gastric and balloon lumens below the most distal gastric port are blocked to any flow. It is believed that appropriate spaced-apart placement of adhesive and resultant flexibility could: facilitate the tube 26 to navigate beyond the Ligament of Treitz; allow for the use of stiffer polymers for the tube 26; and help counter movement of the tube 26 induced by peristaltic action of the muscles of the intestinal tract. Finally, the solidification of the adhesive permanently fixes the new, larger cross-sectional size of the jejunal lumen 44 and the new, reduced cross-sectional size of the gastric and balloon lumens 46, 42 from below the most distal gastric port 28 to the distal end 29 of the tube 26. These new, reduced cross-sectional sized lumens 46, 42 are non-functional lumens.

In order to maintain the exterior, round shape of the tube 26, the tube 26 may further be constrained within a fixture, e.g., a hollow cylinder, during the pressurizing, adhesive adding and solidifying steps. The cross-sectional view of the tube treated according to the previous steps may be seen in FIG. 4. While the gastric-jejunal tube 26 has the same exterior cross-sectional geometry above and below the gastric port 28, the cross-sectional area of the jejunal lumen 44 below the gastric port is increased on the order of approximately 5-15% over the jejunal lumen 44 cross-sectional area above the gastric port 28, more particularly 10 to 15% over the jejunal lumen cross-sectional area above the gastric port. While the different cross-sections can be made via extrusion of separate tubing segments that are subsequently joined together (end to end), the disclosed technique of pressurizing the jejunal lumen 44 and selective filling of portions of the gastric and balloon lumens 46, 42 with adhesive is a preferred fabrication method for the tubing.

This geometry distortion is desirably selectively accomplished only in the portion of the tube 26 that is below the most distal gastric port 28 and/or past the area that would reside in the stomach. The gastric lumen 46 must remain with a relatively large cross-sectional area in the stomach area above (and to) the most distal gastric port 28 in order to effectively deliver medications, etc. to the stomach and aspirate gastric contents, as previously discussed.

It is believed that this geometry distortion can alternatively be completed using a mandrel loaded in the jejunal lumen to distort the shape. The mandrel could have lubricious surface to help load and unload from the tubing. It could also be loaded and unloaded to/from the mandrel using air pressure to create the lubricity.

It was also found during development that the cross-sectional geometry distortions are harder to achieve in silicone (the prior art material). This is believed to be due to the type of silicone tubing that is suitable for the device. Such tubing has a thicker wall because silicone is relatively softer than polyurethane. As a consequence, it is desired to use polyurethane tubing to help maximize the cross-sectional area. A particularly suitable polymer is Lubrizol's thermoplastic polyurethane elastomer TECOFLEX® EG80A HNCO having a Shore A hardness of 72A. This choice of material is not meant to be limiting and is only provided as an example. The choice of materials involves a trade-off between stiffness to avoid the collapse of the lumens inside the tube and softness to allow the tube to successfully bend beyond the ligament of Treitz. Should newer materials be developed that provide a more desirable balance of stiffness and softness, their use is contemplated herein. Also, as discussed above, discontinuous placement of the adhesive may allow for stiffer materials to be used for the tube.

Hardness is measured using a device called a "durometer", an instrument specifically developed to measure relative hardness, and is usually performed following ASTM D2240. In the Shore A and D hardness or durometer scales, a higher number indicates a polymer that is harder than a polymer having a lower number within each scale. The Shore A and D scales are used for different types of polymers. Typically the Shore A scale is used for softer, more elastic polymers and the Shore D scale used for stiffer polymers. When comparing the Shore A and Shore D scales, low D values are typically harder than high A values. For example, a 55D hardness is typically harder than a 90A shore hardness value.

In addition, the prior art method of using adhesive required long solidifying times. A new adhesive is preferred that requires a short amount of time to solidify. One exemplary adhesive is a polyurethane based UV curable adhesive available from the Dymax Corporation of Torrington, CT under the trade name Dymax 1204-M-SC. Any other suitable adhesive may be used provided it solidifies relatively quickly and is compatible with the materials from which the tube is made. By "solidifies relatively quickly" is meant a material that solidifies in a industrially reasonable time, generally less than one hour and more desirably less than 30 minutes and still more desirably less than 5 minutes. Tungsten 47 is desirably added to the adhesive in an amount of 5 to 25 weight percent in order to provide radio-opacity so that the location of the tube may be visualized after placement.

If additional radio-opacity is desired, additional radio-opaque materials 45 may be added to the adhesive or to the polymer from which the tube is made. Radio-opaque materials are those that absorb and/or block x-rays from passing through an item. These include iodine and barium substances, bismuth salts, tungsten, gold metal, halogenated moieties, metal containing, optically transparent polymers and mixtures thereof. The differential in radio-opacity allows one to discern the position of the tube using x-rays once it is placed in a patient's jejunum.

The additional radio-opaque additive may be present in an amount between 5 and 60 weight percent, more desirably 10 and 40 weight percent or still more desirably between 20 and 30 percent. The radio-opaque additive may be compounded with the polymeric material from which the tube is made in the conventional manner; e.g., barium sulfate powder is compounded into the polymer through extrusion compounding to produce resin pellets at the proper weight percent addition rate.

In still another embodiment, the tungsten or additional radio-opaque material may be added to the adhesive in an intermittent fashion, so that the gastric lumen after treatment has sections that are radio-opaque and sections that are not radio-opaque that alternate along the length of the tube. This could aid in measuring the length of the tube at different points in the intestine.

As used herein and in the claims, the term "comprising" is inclusive or open-ended and does not exclude additional unrecited elements, compositional components, or method steps. While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure.

It is therefore intended that the claims cover all such modifications, alterations and other changes encompassed by the appended claims.

We claim:

1. A gastric jejunal tube, comprising:
a uniform outside diameter along an entire length of the gastric jejunal tube;
an interior gastric lumen open to one or more gastric ports defined in the gastric jejunal tube, and an interior jejunal lumen open to one or more jejunal ports defined in the gastric jejunal tube;
a balloon lumen that is reduced in cross-sectional size from distal to the one or more gastric ports relative to the a cross-sectional size of the balloon lumen proximal to the one or more gastric ports;
an interior wall separating the interior gastric lumen from the interior jejunal lumen;
the interior wall shifting at a location distal to a most distal of the one or more gastric ports such that, at the shift location of the interior wall, the interior gastric lumen decreases in cross-sectional size and the interior jejunal lumen increases in cross-sectional size along a remaining length of the gastric jejunal tube to a distal end of the interior jejunal lumen; and
the interior wall extending at its shifted location to the distal end of the interior jejunal lumen.

2. The gastric jejunal tube as in claim 1, wherein the interior gastric lumen and the interior jejunal lumen are defined along the entire length of the gastric jejunal tube.

3. The gastric jejunal tube as in claim 1, wherein the interior gastric lumen is sealed at the shift location of the interior wall.

4. The gastric jejunal tube as in claim 1, wherein the interior gastric lumen and the balloon lumen are maintained in their respective reduced cross-sectional size by a solidified adhesive in the interior gastric lumen and the balloon lumen.

5. The gastric jejunal tube as in claim 4, wherein the solidified adhesive contains tungsten in an amount between 5 and 25 weight percent.

6. The gastric jejunal tube as in claim 4, wherein the solidified adhesive contains a radio-opaque additive.

7. The gastric jejunal tube as in claim 1, wherein the balloon lumen has an oval shape.

8. The gastric jejunal tube as in claim 1, wherein the interior gastric lumen has a "D" shape.

9. The gastric jejunal tube as in claim 1, wherein the gastric jejunal tube contains a radio-opaque additive.

10. A gastric jejunal device, comprising the gastric jejunal tube of claim 1, a base, and a retention device secured to a portion of the gastric jejunal tube.

* * * * *